(12) United States Patent
Frazier et al.

(10) Patent No.: US 6,231,561 B1
(45) Date of Patent: May 15, 2001

(54) METHOD AND APPARATUS FOR CLOSING A BODY LUMEN

(75) Inventors: Andrew G. C. Frazier, Redwood City; Erik J. van der Burg, Sunnyvale; Michael D. Lesh, Mill Valley, all of CA (US)

(73) Assignee: Appriva Medical, Inc., Sunnyvale, CA (US)

( * ) Notice: Subject to any disclaimer, the term of this patent is extended or adjusted under 35 U.S.C. 154(b) by 0 days.

(21) Appl. No.: 09/399,521

(22) Filed: Sep. 20, 1999

(51) Int. Cl.[7] .................................................. A61M 31/00
(52) U.S. Cl. ............................................................ 604/500
(58) Field of Search .................................... 604/500, 115, 604/117, 507, 511; 606/139

(56) References Cited

U.S. PATENT DOCUMENTS

| | | |
|---|---|---|
| 4,710,192 | 12/1987 | Liotta et al. . |
| 4,950,285 | 8/1990 | Wilk . |
| 4,994,069 | 2/1991 | Ritchart et al. . |
| 5,123,428 | 6/1992 | Schwarz . |
| 5,171,259 | 12/1992 | Inoune . |
| 5,281,238 | 1/1994 | Chin et al. . |
| 5,282,827 | 2/1994 | Kensey et al. . |
| 5,306,234 | 4/1994 | Johnson . |
| 5,373,840 | 12/1994 | Knighton . |
| 5,375,612 | 12/1994 | Cottenceau et al. . |
| 5,403,326 | 4/1995 | Harrison et al. . |
| 5,527,338 | 6/1996 | Purdy . |
| 5,593,422 | 1/1997 | Muijs Van Der Moer et al. . |
| 5,593,424 | 1/1997 | Northrup, III . |
| 5,632,753 | 5/1997 | Loeser . |
| 5,709,224 | 1/1998 | Behl et al. . |
| 5,746,747 | 5/1998 | McKeating . |
| 5,814,068 | 9/1998 | Koike et al. . |
| 5,827,268 | 10/1998 | Laufer . |
| 5,843,118 | 12/1998 | Sepetka et al. . |
| 5,860,991 | 1/1999 | Klein et al. . |
| 5,865,791 | 2/1999 | Whayne et al. . |
| 5,879,366 | 3/1999 | Shaw et al. . |

*Primary Examiner*—John D. Yasko
(74) *Attorney, Agent, or Firm*—Knobbe, Martens, Olson & Bear, LLP (57) ABSTRACT

Disclosed is a closure catheter, for closing a body cavity such as a vessel, or the left atrial appendage of the heart. The closure catheter includes a plurality of deployable tissue anchors, which may be laterally deployed into surrounding tissue. The anchors may thereafter be used to draw the tissue radially inwardly, to close the body cavity. Methods are also disclosed.

4 Claims, 12 Drawing Sheets

METHOD AND APPARATUS FOR CLOSING A BODY LUMEN

The present invention relates to methods and devices for closing a body lumen or cavity and, in particular, for closing the left atrial appendage.

BACKGROUND OF THE INVENTION

Embolic stroke is the nation's third leading killer for adults, and is a major cause of disability. There are over 700,000 strokes per year in the United States alone. Of these, roughly 100,000 are hemoragic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA.

Blackshear and Odell have reported that of the 1288 patients with non-rheumatic atrial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. Ann Thorac. Surg., 1996.61(2):755–9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear and Odell, above. See also Lindsay B D., Obliteration of the Left Atrial Appendage: A Concept Worth Testing, Ann Thorac. Surg., 1996.61(2):515.

Despite the various efforts in the prior art, there remains a need for a minimally invasive method and associated devices for reducing the risk of thrombus formation in the left atrial appendage.

SUMMARY OF THE INVENTION

There is provided in accordance with one aspect of the present invention, a closure catheter for closing an opening in tissue, a body lumen, hollow organ or other body cavity. The catheter and methods of its use are useful in a variety of procedures, such as treating (closing) wounds and naturally or surgically created apertures or passageways. Applications include, but are not limited to, atrial septal defect closure, patent ductus arteriosis closure, aneurysm isolation and graft and/or bypass anostomosis procedures.

The closure catheter comprises an elongate, flexible catheter body, having a proximal end and a distal end, and a longitudinal axis extending therebetween. At least two anchor supports are provided on the distal end. The anchor supports are movable between a first position in which they are substantially parallel with the axis, and a second position in which they are inclined laterally from the axis. A control is provided on the proximal end for moving the anchor supports from the axial orientation into the inclined orientation.

Preferably, from about four anchor supports to about eight anchor supports are provided. At least one, and preferably all, of the anchor supports comprises a tube, having a tissue anchor movably positioned within the tube.

There is provided in accordance with another aspect of the present invention, a catheter for deploying at least one tissue anchor at an angle to the longitudinal axis of the catheter and into an adjacent tissue surface. The catheter comprises an elongate flexible body, having a proximal end and a distal end. At least one anchor support is provided on the body, and is movable between an axial orientation and an inclined orientation. A control is provided on the body for controlling movement of the anchor support between the axial orientation and the inclined orientation. At least one anchor is movably carried by the anchor support.

In one embodiment, the anchor support is biased towards the inclined orientation. The control comprises an axially movable actuator, for moving the anchor support between the axial orientation and the inclined orientation. The actuator comprises a core connected to the anchor support such that axial movement of the core advances the anchor support from the axial orientation to the inclined orientation.

In one embodiment, each anchor support removably carries an introducer which is removably connected to the anchor for driving the anchor into the tissue. The anchor comprises a tubular body, for slideably receiving the introducer therethrough.

In accordance with a further aspect of the present invention, there is provided a method of securing a plurality of tissue anchors about the interior circumference of a tubular tissue structure. The method comprises the steps of providing a tissue anchor delivery catheter having a plurality of anchor supports movable between an axial orientation and an inclined orientation. An anchor is carried by each anchor support, each anchor having a suture secured thereto. The catheter is transluminally advanced to a target site within a tubular tissue structure while the anchor supports are in the axial orientation. The anchor supports are advanced from the axial orientation to the inclined orientation at a target site, and anchors are deployed from the anchor supports into the tissue.

In one embodiment, the advancing the anchor support step comprises axially moving a control on the catheter.

Following securing the plurality of tissue anchors into the tissue, the method may additionally comprise the step of proximally retracting the sutures to draw the anchors radially inwardly towards each other to close the tubular tissue structure. In one application of the invention, the tubular tissue structure comprises the left atrial appendage.

In accordance with a further aspect of the present invention, there is provided a method of reducing the volume of the left atrial appendage. The method comprises the steps of providing a catheter having at least four tissue anchors thereon, the anchors each having a suture secured thereto. The catheter is advanced through the heart and into the left atrial appendage. The anchors are inclined radially outwardly from the axis of the catheter, towards the tissue surrounding the opening to the left atrial appendage. The anchors are deployed from the catheter and into the tissue, and the sutures are retracted to reduce the volume of the left atrial appendage.

Preferably, the inclining step comprises proximally retracting a control for inclining anchor supports which carry the anchors. In one embodiment, proximally retracting the control axially compresses the anchor support such that the anchors incline radially outwardly from the axis of the catheter.

Further features and advantages of the present invention will become apparent to those of skill in the art in view of the detailed description of the preferred embodiment which follows, when considered together with the attached drawings and claims.

DETAILED DESCRIPTION OF THE PREFERRED EMBODIMENT

For simplicity, the present invention will be described primarily in the context of a left atrial appendage closure procedure. However, the device and methods herein are readily applicable to a wider variety of closure or attachment procedures, and all such applications are contemplated by the present inventors. For example, additional heart muscle procedures such as atrial septal defect closure and patent ductus arteriosis closure are contemplated. Vascular procedures such as isolation or repair of aneurysms, anastomosis of vessel to vessel or vessel to prosthetic tubular graft (e.g., PTFE or Dacron tubes, with or without wire support structures as are well known in the art) joints may also be accomplished using the devices of the present invention. Attachment of implantable prostheses, such as attachment of the annulus of a prosthetic tissue or mechanical heart valve may be accomplished. A variety of other tissue openings, lumens, hollow organs and surgically created passageways may be closed, patched or reduced in volume in accordance with the present invention. For example, an opening in a tissue plane may be closed or patched, such as by attaching a fabric or tissue sheet across the opening. In one specific application, the device of the present invention is used to anchor a fabric patch to close an atrial septal defect. The target aperture or cavity may be accessed transluminally (e.g., vascular catheter or endoscope) or through solid tissue, such as transmural, percutaneous or other approach. The present invention may also be used in an open surgical procedure such as to close the left atrial appendage during open heart surgery to correct or address a different condition. In another example, the device is advanced through the percutaneous opening and used to close a vascular puncture such as a femoral artery access site for a PTA or other diagnostic or therapeutic interventional procedure. Adaptation of the devices and methods disclosed herein to accomplish procedures such as the foregoing will be apparent to those of skill in the art in view of the disclosure herein.

Figure 1:
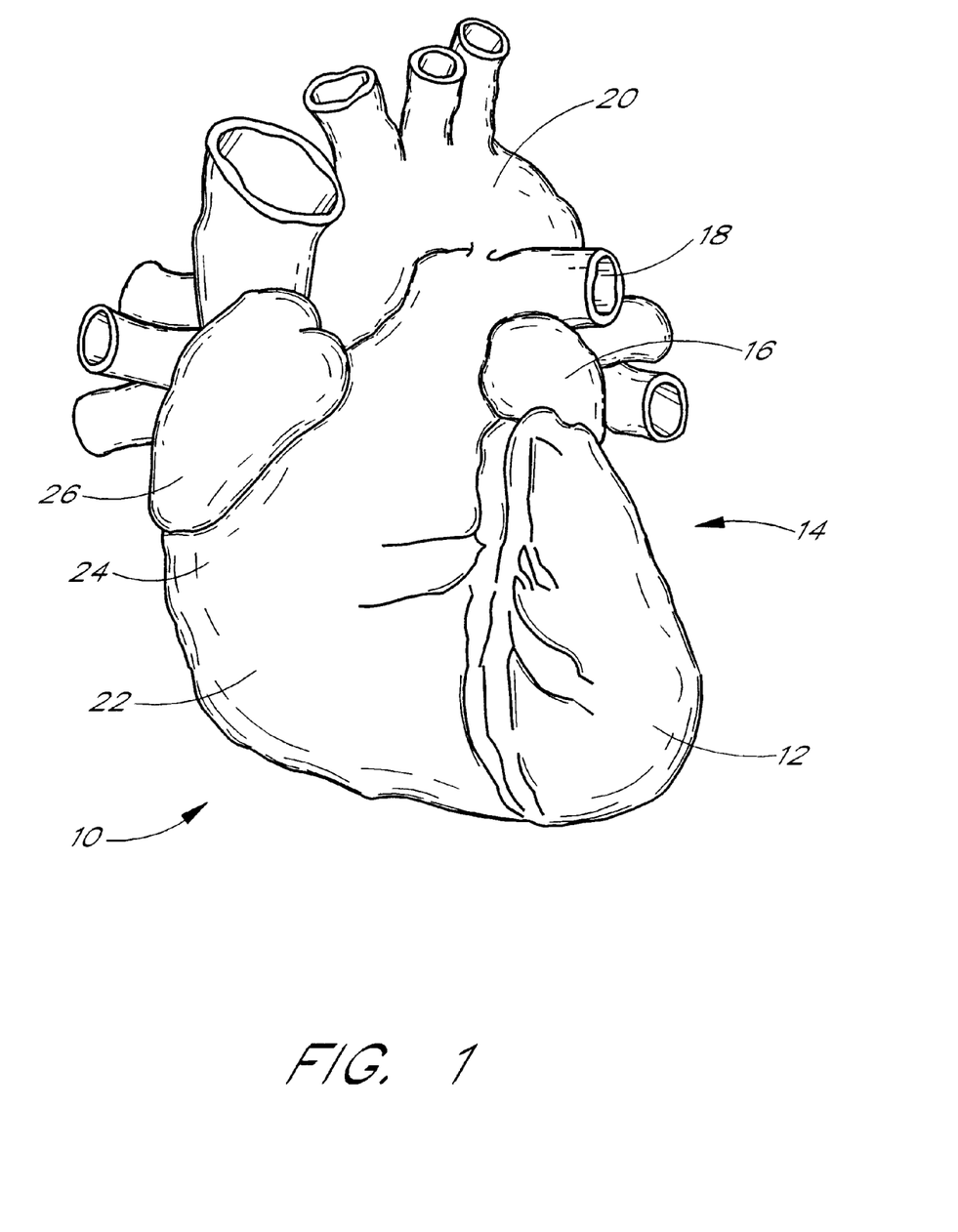
FIG. 1 is an anterior illustration of a heart, with the proximal parts of the great vessels.

Referring to FIG. 1, a heart 10 is illustrated to show certain portions including the left ventricle 12, the left atrium 14, the left atrial appendage (LAA) 16, the pulmonary artery 18, the aorta 20, the right ventricle 22, the right atria 24, and the right atrial appendage 26. As is understood in the art, the left atrium 14 is located above the left ventricle 12 and the two are separated by the mitral valve (not illustrated). The LAA 16 is normally in fluid communication with the left atrium 14 such that blood flows in and out of the LAA 16 as the heart 10 beats.

In accordance with the present invention, a closure catheter 38 is advanced through the heart and into the LAA. In general, the closure catheter 38 is adapted to grasp tissue surrounding the opening to the LAA, and retract it radially inwardly to reduce the volume of and/or close the LAA. The LAA is thereafter secured in its closed orientation, and the closure catheter 38 is removed. Specific aspects of one embodiment of the closure catheter in accordance with the present invention are described in greater detail below.

The LAA may be accessed through any of a variety of pathways as will be apparent to those of skill in the art. Transeptal access, as contemplated by FIG. 2, may be achieved by introducing a transeptal catheter through the femoral or jugular vein, and transluminally advancing the catheter into the right atrium. Once in the right atrium, a long hollow needle with a preformed curve and a sharpened distal tip is forcibly inserted through the fossa ovalis. A radiopaque contrast media may then be injected through the needle to allow visualization and ensure placement of the needle in the left atrium, as opposed to being in the pericardial space, aorta, or other undesired location.

Figure 2:
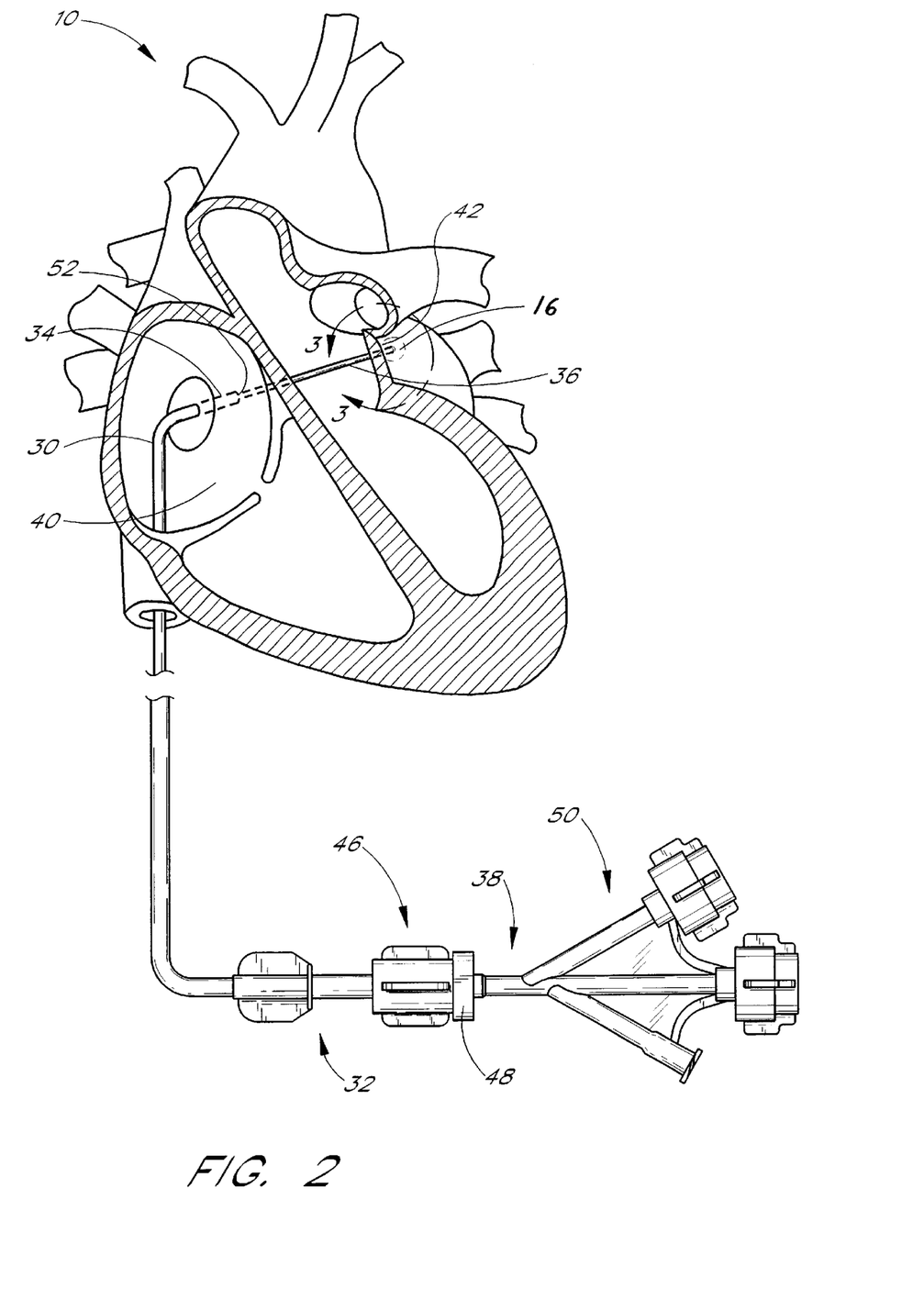
FIG. 2 is a schematic cross section through the heart with a transeptal catheter deployed through the septum and a closure catheter extending into the LAA.

Once the position of the needle in the left atrium is confirmed, the transeptal catheter is advanced into the left atrium. The closure catheter 38 may then be advanced through the transeptal catheter 30, and steered or directed into the left atrial appendage. Alternative approaches include venous transatrial approaches such as transvascular advancement through the aorta and the mitral valve. In addition, the devices of the present invention can be readily adapted for use in an open heart surgical procedure, although transluminal access is presently preferred.

Thus, referring to FIG. 2, a transeptal catheter 30 has a proximal end 32 and a distal end 34. The distal end 34 of the transeptal catheter 30 has breached the septum 40 of the patient's heart 10 and is disposed adjacent the opening 42 of the patient's LAA 16. The distal end 36 of a closure catheter 38 extends from the distal end 34 of the transeptal catheter 30 and into the LAA 16.

At the proximal end 46 of the transeptal catheter 30, a luer connector coupled to a hemostasis valve 48 prevents the egress of blood from a central lumen of the transeptal catheter 30. The proximal end 50 of the closure catheter 38 extends proximally from the hemostasis valve 48. Additional details concerning the use and design of transeptal access catheters are well known in the art and will not be discussed further herein.

Figure 3A:
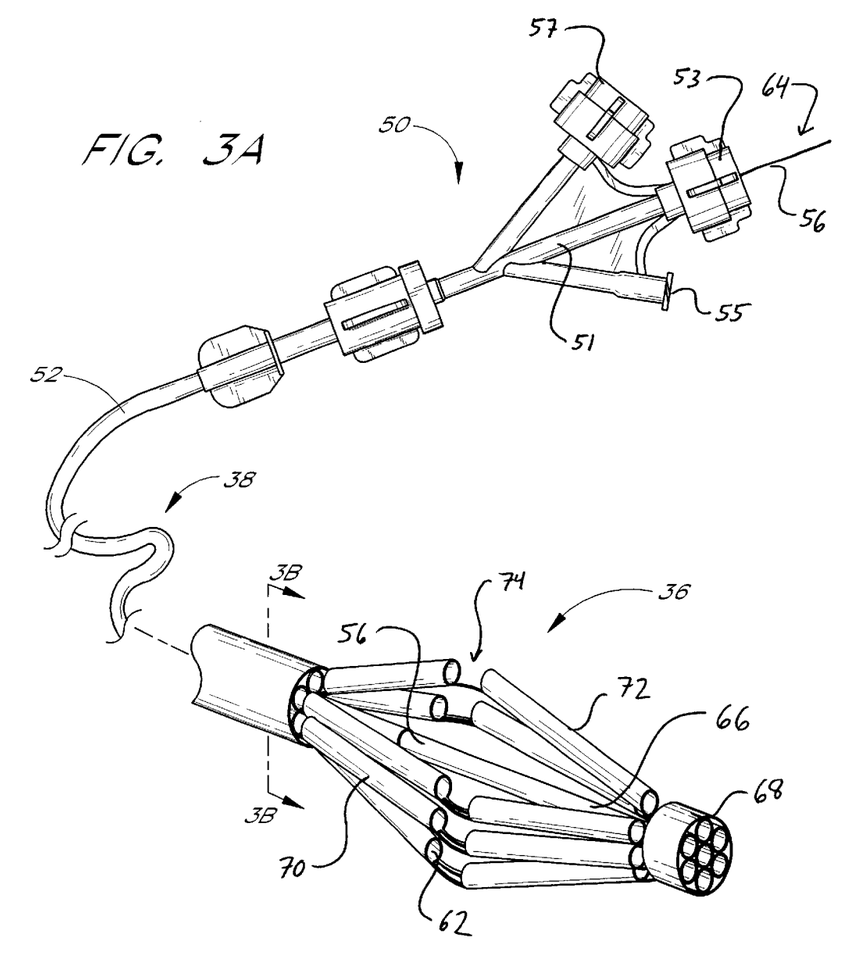
FIG. 3A is an enlarged perspective view of the distal end of a closure catheter in accordance with the present invention.
Figure 3B:
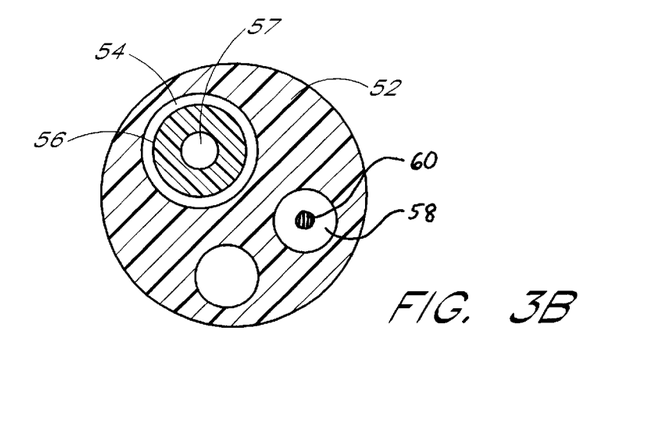
FIG. 3B is a cross section taken along the lines 3B—3B of FIG. 3A.

Referring to FIGS. 2 and 3, the closure catheter 38 thus has a proximal end 50, a distal end 36, and an elongate flexible tubular body 52 extending therebetween. The axial length of the closure catheter 38 can be varied, depending upon the intended access point and pathway. For a femoral vein-transeptal approach, the closure catheter 38 generally has an axial length within the range of from about 100 cm to about 140 cm, and, in one embodiment, about 117 cm.

The outside diameter of the flexible body 52 can also be varied, depending upon the number of internal lumen and other functionalities as will be understood by those of skill in the art. In one embodiment, the outside diameter is about 12 FR (0.156 inches), and closure catheters are contemplated to have OD's generally within the range of from about 0.078 inches to about 0.250 inches. Diameters outside of the above range may also be used, provided that the functional consequences of the diameter are acceptable for the intended application of the catheter.

For example, the lower limit of the outside diameter for tubular body 52 in a given application will be a function of the number of fluid or other functional lumen contained within the catheter. In addition, tubular body 52 must have sufficient pushability to permit the catheter to be advanced to its target location within the heart without buckling or undesirable bending. The ability of the tubular body 52 to transmit torque may also be desirable, such as in embodiments in which the tissue anchor deployment guides are not uniformly circumferentially distributed about the distal end 36 of the catheter. Optimization of the outside diameter of the catheter, taking into account the flexibility, pushability and torque transmission characteristics can be accomplished through routine experimentation using conventional catheter design techniques well known to those of skill in the art.

The flexible body 52 can be manufactured in accordance with any of a variety of known techniques. In one embodiment, the flexible body 52 is extruded from any of a variety of materials such as HDPE, PEBAX, nylon, polyimide, and PEEK. Alternatively, at least a portion or all of the length of tubular body 52 may comprise a spring coil, solid walled hypodermic needle or other metal tubing, or braided reinforced wall, as are known in the art.

The proximal end 50 of the closure catheter 38 is provided with a manifold 51, having a plurality of access ports. Generally, manifold 51 is provided with an access port 53 which may be used as a guidewire port in an over the wire embodiment, and a deployment wire port 57. Additional access ports such as a contrast media introduction port 55, or others may be provided as needed, depending upon the functional requirements of the catheter.

The tubular body 52 has at least a first actuator lumen 54, for axially movably receiving an actuator 56. Actuator 56 extends between a proximal end 64 at about the proximal end of the closure catheter, and a distal end 66 at or near the distal end 36 of the closure catheter 38. The distal end 66 of the actuator 56 is secured to a cap 68. In the illustrated embodiment, the actuator lumen 54 is in communication with the access port 53 to permit the actuator 56 to extend proximally therethrough.

Actuator 56 can have a variety of forms, depending upon the construction of the anchor supports 62 on the distal end 36 of the closure catheter 38. In general, the catheter in the area of the anchor supports 62 should have a crossing profile of no more than about 14 French for transluminal advancement and positioning. However, the anchor supports must then be capable of directing tissue anchors into the wall of the cavity or lumen which may have an inside diameter on the order of about 1.5 cm to about 3 cm in the case of the LAA in an average adult. The device of the present invention can be readily scaled up or down depending upon the intended use, such as to accommodate a 5 cm to 10 cm cavity in GI tract applications or 5 mm to about 2 cm for vascular applications. For this purpose, the anchor supports are preferably moveable between a reduced cross sectional orientation and an enlarged cross sectional orientation to aim at, and, in some embodiments, contact the target tissue surface.

One convenient construction to accomplish the foregoing is for each anchor support 62 to take the form of a lever arm structure which is pivotably connected at one end to the catheter body. This construction permits inclination of the anchor support throughout a continuous range of outside diameters which may be desirable to aim the anchor and accommodate different treatment sites and/or normal anatomical variation within the patient population.

A laterally moveable anchor support can be moved between an axial orientation and an inclined orientation in a variety of ways. One convenient way is through the use of a pull wire or other actuator which increases the diameter of the deployment zone of the catheter in response to an axial shortening of fixed length moveable segments as disclosed in more detail below. For this construction, the actuator will be under pulling tension during actuation. Any of a variety of structures such as polymeric or metal single or multiple strand wires, ribbons or tubes can be used. In the illustrated embodiment, the actuator 56 comprises stainless steel tube, having an outside diameter of about 0.025 inches.

A pull wire can alternatively be connected to the radially outwardly facing surface and preferably near the distal end of each anchor support, and each anchor support is hingably attached at its proximal end to the catheter. Proximal traction on the pull wire will cause the anchor support to incline radially outwardly in the distal direction, and toward the target tissue.

In an alternate construction, the anchor support is inclined under a compressive force on the actuator 56. For example, the embodiment described in detail below can readily be converted to a push actuated system by axially immovable fixing the distal end of the anchor guide assembly to the catheter and slideably pushing the proximal end of the anchor guide assembly in the distal direction to achieve axial compression as will become apparent from the discussion below.

Push wire actuators have different requirements, than pull actuator systems, such as the ability to propagate a sufficient compressive force without excessive compression bending or friction. Thus, solid core wires or tubular structures may be preferred, as well as larger outside diameters compared to the minimum requirements in a pull actuated system. Thus, the inside diameter of the actuator lumen 57 may be varied, depending upon the actuator system design. In the illustrated embodiment, the actuator lumen 57 has an ID of about 0.038 inches, to slideably accommodate the 0.025 inch OD actuator 56.

A radially outwardly directed force on the anchor supports 62 can be provided by any of a variety of alternative expansion structures, depending upon desired performance and construction issues. For example, an inflatable balloon can be positioned radially inwardly from a plurality of hingably mounted anchor supports 62, and placed in communication with actuator lumen 54 which may be used as an inflation lumen. Any of a variety of balloon materials may be used, ranging in physical properties from latex for a highly compliant, low pressure system to PET for a non-compliant high pressure and consequently high radial force system, as is understood in the balloon angioplasty arts.

The tubular body 52 may additionally be provided with a guidewire lumen 57, or a guidewire lumen 57 may extend coaxially throughout the length of a tubular actuator 56 as in the illustrated embodiment.

The tubular body 52 may additionally be provided with a deployment lumen 58, for axially movably receiving one or more deployment elements 60 such as a wire, or suture for deploying one or more tissue anchors 90 into the target tissue 110. Deployment force for deploying the tissue anchors 90 can be designed to be in either the distal or proximal direction, and many of the considerations discussed above in connection with the actuator 56 and corresponding actuator lumen 54 apply to the deployment system as well. In the illustrated embodiment, deployment of the tissue anchors 90 is accomplished by proximal retraction on the deployment element 60 which, in turn, retracts deployment wire 106. Pushability is thus not an issue, and common suture such as 0.008 inch diameter nylon line may be used. For this embodiment, deployment lumen 58 has an inside diameter of about 0.038 inches. The deployment lumen 58 can be sized to receive either a single deployment element 60, or a plurality of deployment elements 106 such as a unique suture for each tissue anchor.

The distal end 36 of the closure catheter 38 is provided with one or more anchor supports 62, for removably carrying one or more tissue anchors. Preferably, two or more anchor supports 62 are provided, and, generally, in a device intended for LAA closure, from about 3 to about 12 anchor supports 62 are provided. In the illustrated embodiment, six anchor supports 62 are evenly circumferentially spaced around the longitudinal axis of the closure catheter 38.

Each anchor support 62 comprises a surface 63 for slideably retaining at least one tissue anchor, and permitting the tissue anchor to be aimed by manipulation of a control on the proximal end 50 of the closure catheter 38. Specific details of one embodiment of the anchor support 62 having a single anchor therein will be discussed below. Multiple anchors, such as two or three or more, can also be carried by each anchor support for sequential deployment.

The anchor supports 62 are movable between an axial orientation and an inclined orientation, in response to manipulation of a proximal control. The proximal control can take any of a variety of forms, such as slider switches or levers, rotatable levers or knobs, or the like, depending upon the desired performance. For example, a rotatable knob control can permit precise control over the degree of inclination of the anchor supports 62. A direct axial slider control, such as a knob or other grip directly mounted to the actuator 56 will optimize tactile feedback of events such as the anchor supports 62 coming into contact with the target tissue.

Each of the illustrated anchor supports 62 comprises at least a proximal section 70, a distal section 72, and a flex point 74. See FIG. 4. The distal end 73 of each distal section 72 is movably connected to the catheter body or the cap 68. In this embodiment, proximal retraction of the actuator 56 shortens the axial distance between the proximal end 71 of the proximal section 70 and the distal end 73 of distal section 72, forcing the flex point 74 radially outwardly from the longitudinal axis of the closure catheter 38. In this manner, proximal retraction of the actuator 56 through a controlled axial distance will cause a predictable and controlled increase in the angle between the proximal and distal sections 70 and 72 of the anchor support 62 and the longitudinal axis of the catheter. This is ideally suited for aiming a plurality of tissue anchors at the interior wall of a tubular structure, such as a vessel or the left atrial appendage.

Figure 4:
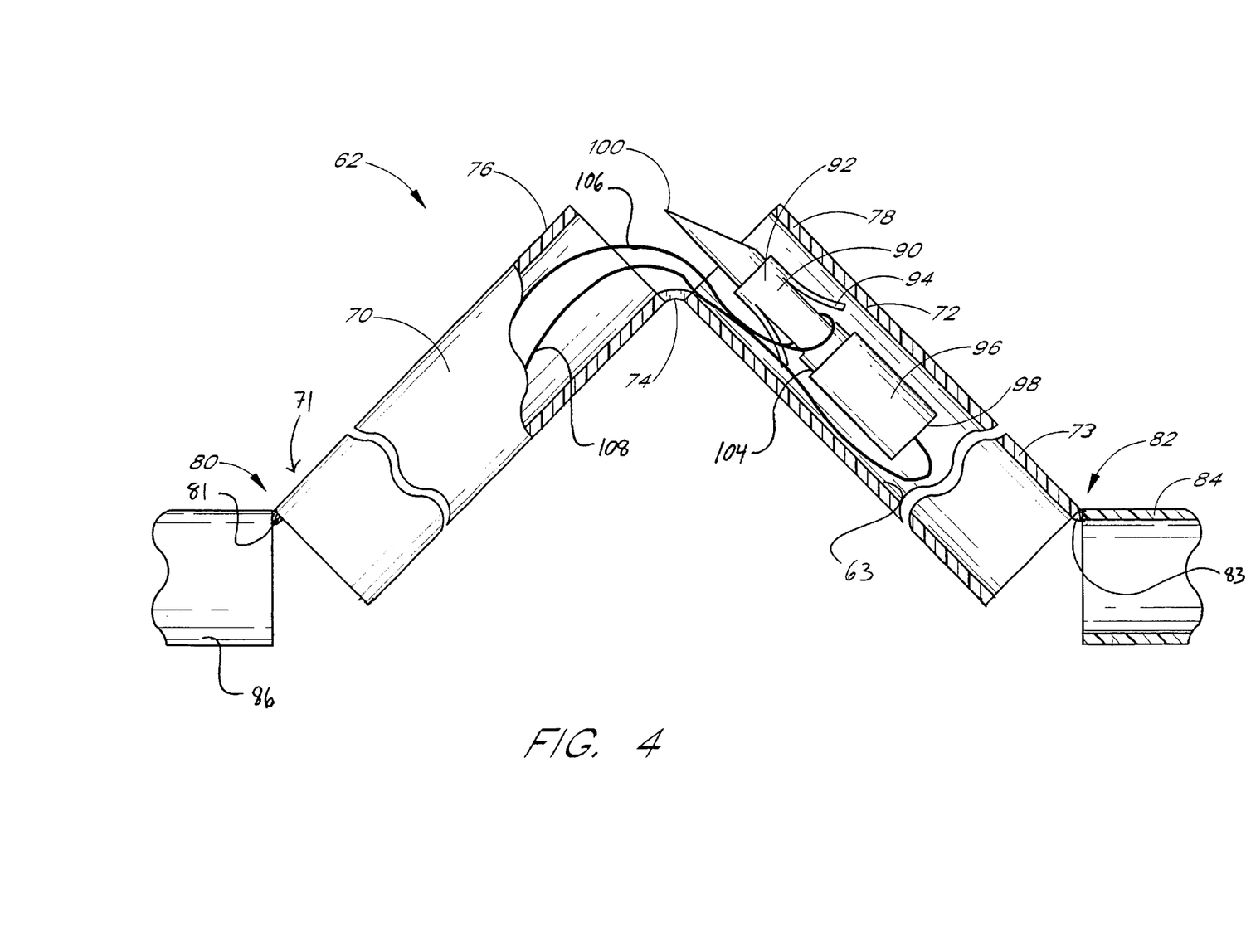
FIG. 4 is a partial cross-sectional view of a tissue anchor and introducer, positioned within an anchor guide in accordance with the present invention.

Referring to FIG. 4, there is illustrated an enlarged detailed view of one anchor support 62 in accordance with the present invention. The proximal section 70 and distal section 72 preferably comprise a tubular wall 76 and 78 joined at the flex point 74. In one embodiment, the proximal section 70 and distal section 72 may be formed from a single length of tubing, such as by laser cutting, photolithography, or grinding to separate the proximal section 70 from the distal section 72 while leaving one or two or more integrally formed hinges at flex point 74. Any of a variety of polymeric or metal tubing may be utilized for this purpose, including stainless steel, Nitinol or other super-elastic alloys, polyimide, or others which will be appreciated by those of skill in the art in view of the disclosure herein.

In the illustrated six tube embodiment, the proximal section 70 and distal section 72 are formed from a length of PEEK tubing having an inside diameter of about 0.038 inches, an outside diameter of about 0.045 inches and an overall length of about 1.4 inches. In general, if more than six anchor supports 62 are used, the diameter of each will be commensurately less than in the six tube embodiment for any particular application. When the proximal section 70 and the distal section 72 are coaxially aligned, a gap having an axial length of about 0.030 is provided therebetween. In the illustrated embodiment, the proximal section 70 and distal section 72 are approximately equal in length although dissimilar lengths may be desirable in certain embodiments. The length of the portion of the anchor support 62 which carries the tissue anchor 90 is preferably selected for a particular procedure or anatomy so that the anchor support 62 will be inclined at an acceptable launch angle when the deployment end of the anchor support 62 is brought into contact with the target tissue 110. Lengths from the hinge to the deployment end of the anchor support 62 within the range of from about 0.5 cm to about 1.5 cm are contemplated for the LAA application disclosed herein.

For certain applications, the proximal section 70 is at least about 10% and preferably at least about 20% longer than the distal section 72. For example, in one device adapted for the LAA closure application, the proximal section 70 in a six anchor device has a length of about 0.54 inches, and the distal section 72 has a length of about 0.40 inches. Each anchor support has an OD of about 0.045 inches. As with previous embodiments, the functional roles and/or the dimensions of the proximal and distal sections can be reversed and remain within the scope of the present invention. Optimization of the relative lever arm lengths can be determined for each application taking into account a variety of variables such as desired device diameter, target lumen or tissue aperture diameter, launch angle and desired pull forces for aiming and deployment.

The proximal end 71 of the proximal section 70 and distal end 73 of distal section 72 are movably secured to the closure catheter 38 in any of a variety of ways which will be apparent to those of skill in the art in view of the disclosure herein. In the illustrated embodiment, each anchor support 62 comprises a four segment component which may be constructed from a single length of tubing by providing an intermediate flex point 74, a proximal flex point 80 and a distal flex point 82. Distal flex point 82 provides a pivotable connection between the anchor support 62 and a distal connection segment 84. The distal connection segment 84 may be secured to the distal end of actuator 56 by any of a variety of techniques, such as soldering, adhesives, mechanical interfit or others, as will be apparent to those of skill in the art. In the illustrated embodiment, the distal connection segment 84 is secured to the distal end 66 of the actuator 56 by adhesive bonding.

The proximal flex point 80 in the illustrated embodiment separates the proximal section 70 from a proximal connection segment 86, which is attached to the catheter body 52. In this construction, proximal axial retraction of the actuator 56 with respect to the tubular body 52 will cause the distal connection segment 84 to advance proximally towards the proximal connection segment 86, thereby laterally displacing the flex point 74 away from the longitudinal axis of the closure catheter 38. As a consequence, each of the proximal section 70 and the distal section 72 are aimed at an angle which is inclined outwardly from the axis of the closure catheter 38.

In general, each flex point 80, 82 includes a hinge 81, 83 which may be, as illustrated, a strip of flexible material. The hinges 81 and 83 are preferably positioned on the inside radius of the flex points 80, 82, respectively, for many construction materials. For certain materials, such as Nitinol or other superelastic alloys, the hinges 81 and 83 can be positioned at approximately 90° or 180° or other angle around the circumference of the tubular anchor guide from the inside radius of the flex point.

Figure 5:
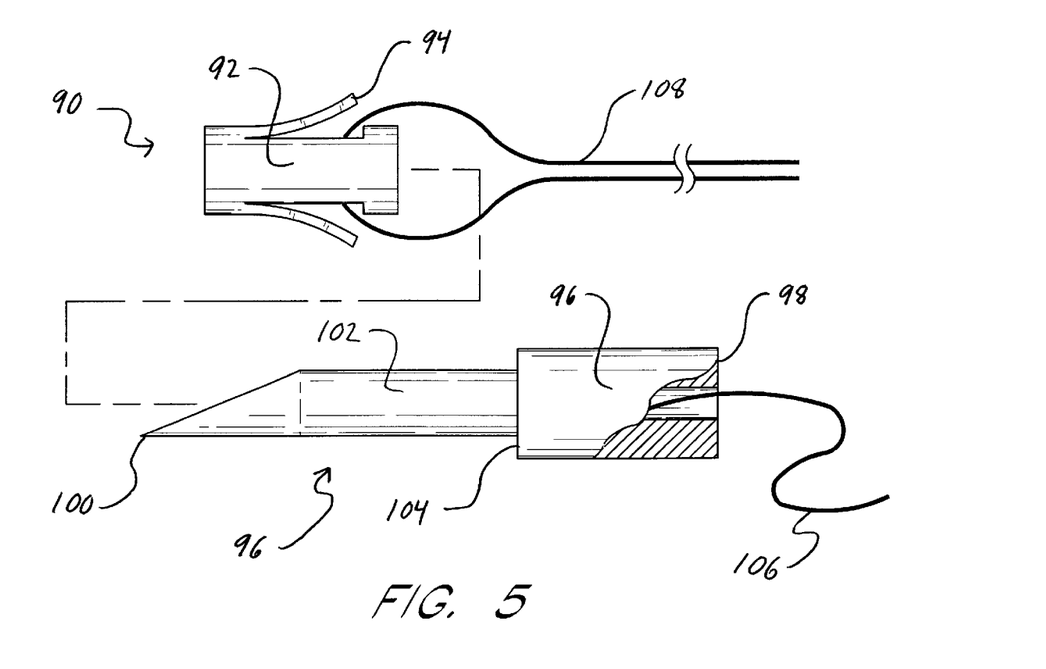
FIG. 5 is an exploded view of a tissue anchor and introducer in accordance with one aspect of the invention.

A tissue anchor 90 is illustrated as positioned within the distal section 72, for deployment in a generally proximal direction. Alternatively, the anchor 90 can be loaded in the proximal section 70, for distal deployment. A variety of tissue anchors can be readily adapted for use with the closure catheter 38 of the present invention, as will be appreciated by those of skill in the art in view of the disclosure herein. In the illustrated embodiment, the tissue anchor 90 comprises a tubular structure having a body 92, and one or more barbs 94. Tubular body 92 is coaxially movably disposed about an introducer 96. Introducer 96 has a proximal section 98, and a sharpened distal tip 100 separated by an elongate distal section 102 for slideably receiving the tissue anchor 90 thereon.

The tissue anchor 90 in the illustrated embodiment comprises a tubular body 92 having an axial length of about 0.118 inches, an inside diameter of about 0.017 inches and an outside diameter of about 0.023 inches. Two or more barbs 94 may be provided by laser cutting a pattern in the wall of the tube, and bending each barb 94 such that it is biased radially outwardly as illustrated. The tissue anchor 90 may be made from any of a variety of biocompatible metals such as stainless steel, Nitinol, Elgiloy or others known in the art. Polymeric anchors such as HDPE, nylon, PTFE or others may alternatively be used. For embodiments which will rely upon a secondary closure structure such as staples, sutures or clips to retain the LAA or other cavity closed, the anchor may comprise a bioabsorbable or dissolvable material so that it disappears after a period of time. An anchor suture 108 is secured to the anchor.

In one embodiment of the invention, the introducer 96 has an axial length of about 0.250 inches. The proximal section 98 has an outside diameter of about 0.023 inches and an axial length of about 0.100 inches. The distal section 102 has an outside diameter of about 0.016 inches and an axial length of about 0.150 inches. The outside diameter mismatch between the proximal section 98 and the distal section 102 provides a distally facing abutment 104, for supporting the tubular body 92 of tissue anchor 90, during the tissue penetration step. A deployment wire (e.g., a suture) 106 is secured to the proximal end 98 of the introducer 96. The introducer 96 may be made in any of a variety of ways, such as extrusion or machining from stainless steel tube stock.

Figure 6A:
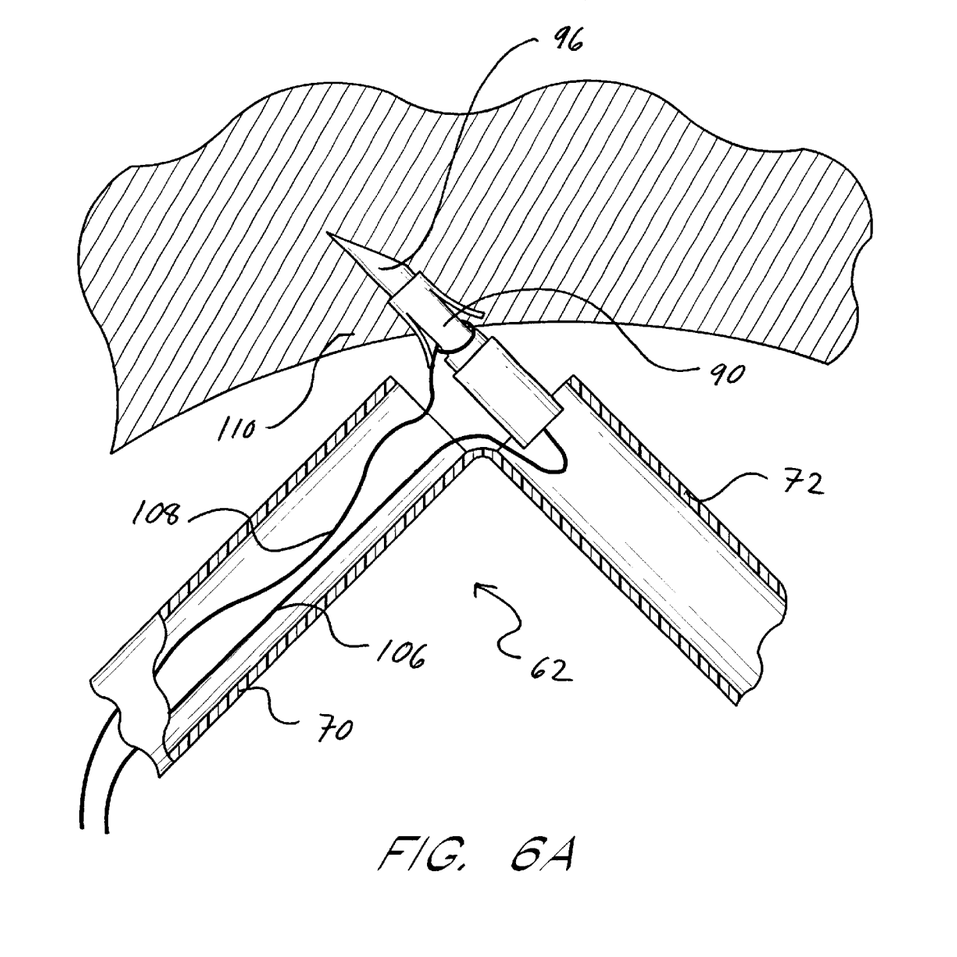
FIG. 6A is a schematic illustration of a tissue anchor and introducer advancing into a tissue surface.
Figure 6B:
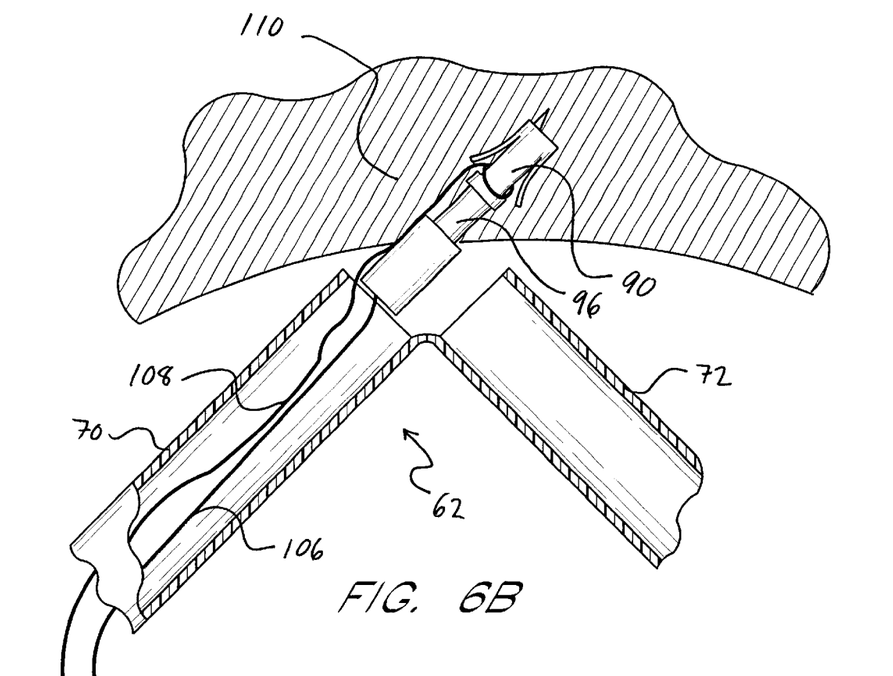
FIG. 6B is an illustration as in FIG. 6A, with the anchor positioned within the tissue and the introducer partially retracted.
Figure 6C:
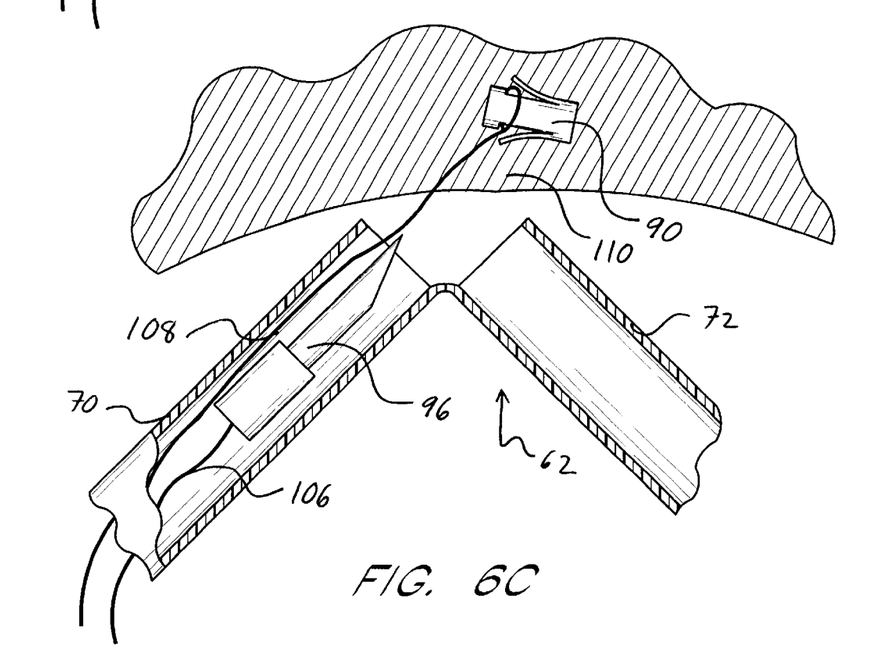
FIG. 6C is an illustration as in FIG. 6B, with the introducer fully retracted and the anchor positioned within the tissue.

Referring to FIGS. 6A–6C, introduction of the tissue anchor 90 into target tissue 110 is illustrated following inclination of the anchor support 62 with respect to the longitudinal axis of the closure catheter 38. Proximal retraction of the deployment wire 106 causes the tissue anchor 90 and introducer 96 assembly to travel axially through the distal section 72, and into the tissue 110. Continued axial traction on the deployment wire 106 causes the longitudinal axis of the introducer 96 to rotate, such that the introducer 96 becomes coaxially aligned with the longitudinal axis of the proximal section 70. Continued proximal traction on the deployment wire 106 retracts the introducer 96 from the tissue anchor 90, leaving the tissue anchor 90 in place within the tissue. The anchor suture 108 remains secured to the tissue anchor 90, as illustrated in FIG. 6C.

Figure 7:
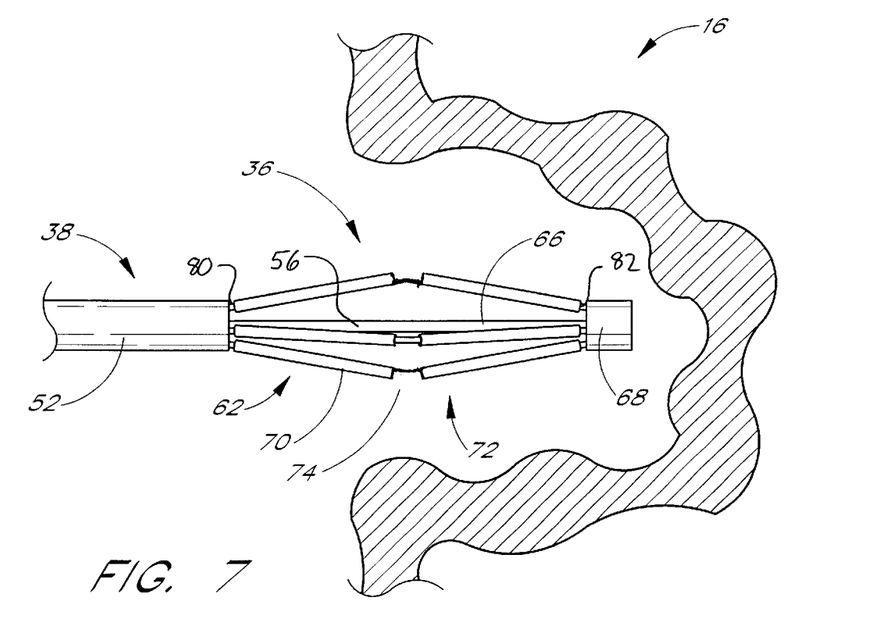
FIG. 7 shows a schematic view of a closure catheter disposed within the opening of the LAA.
Figure 8:
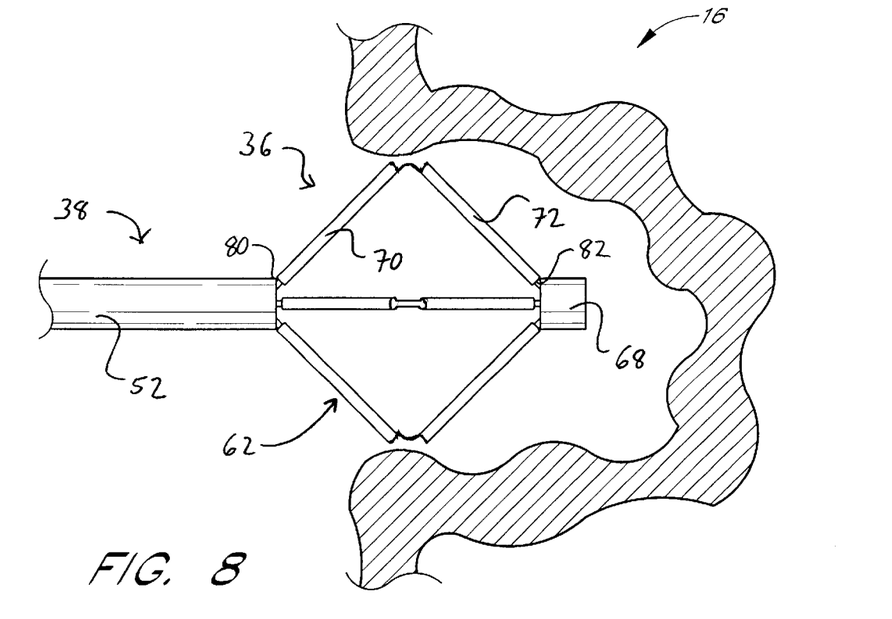
FIG. 8 is a schematic illustration of the opening of the LAA as in FIG. 7, with the anchor guides in an inclined orientation.

In use, the closure catheter 38 is percutaneously introduced into the vascular system and transluminally advanced into the heart and, subsequently, into the left atrial appendage using techniques which are known in the art. Referring to FIG. 7, the distal end 36 of the closure catheter 38 is positioned at about the opening of the LAA 16, and the position may be confirmed using fluoroscopy, echocardiography, or other imaging. The actuator 56 is thereafter proximally retracted, to incline the anchor supports 62 radially outwardly from the longitudinal axis of the closure catheter 38, as illustrated in FIG. 8. Preferably, the axial length of the proximal section 70 of each anchor support 62, in combination with the angular range of motion at the proximal flex point 80, permit the flex point 74 to be brought into contact with the tissue surrounding the opening to the LAA. In general, this is preferably accomplished with the distal section 72 inclined at an angle within a range of from about 45° to about 120° with respect to the longitudinal axis of the closure catheter 38. Actuator 56 may be proximally retracted until the supports 62 are fully inclined, or until tactile feedback reveals that the anchor supports 62 have come into contact with the surrounding tissue 110.

Figure 9:
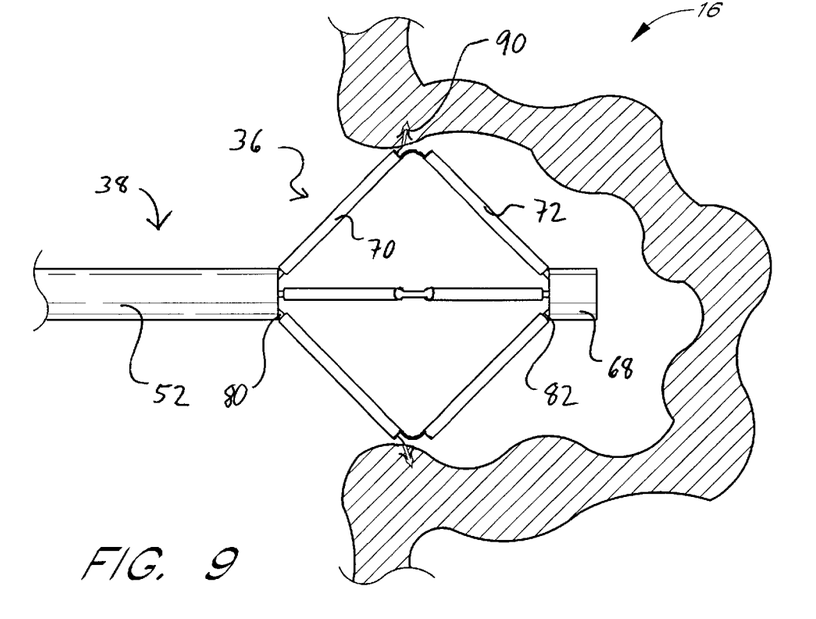
FIG. 9 is a schematic illustration as in FIG. 8, with tissue anchors deployed from the anchor guides.
Figure 10:
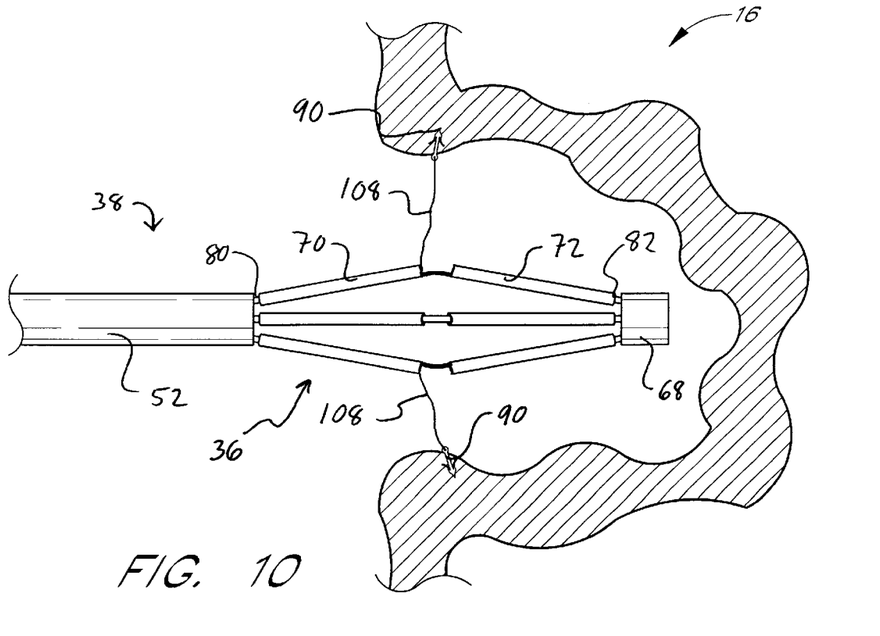
FIG. 10 is a schematic illustration as in FIG. 9, with the anchor guides retracted into an axial orientation.
Figure 11:
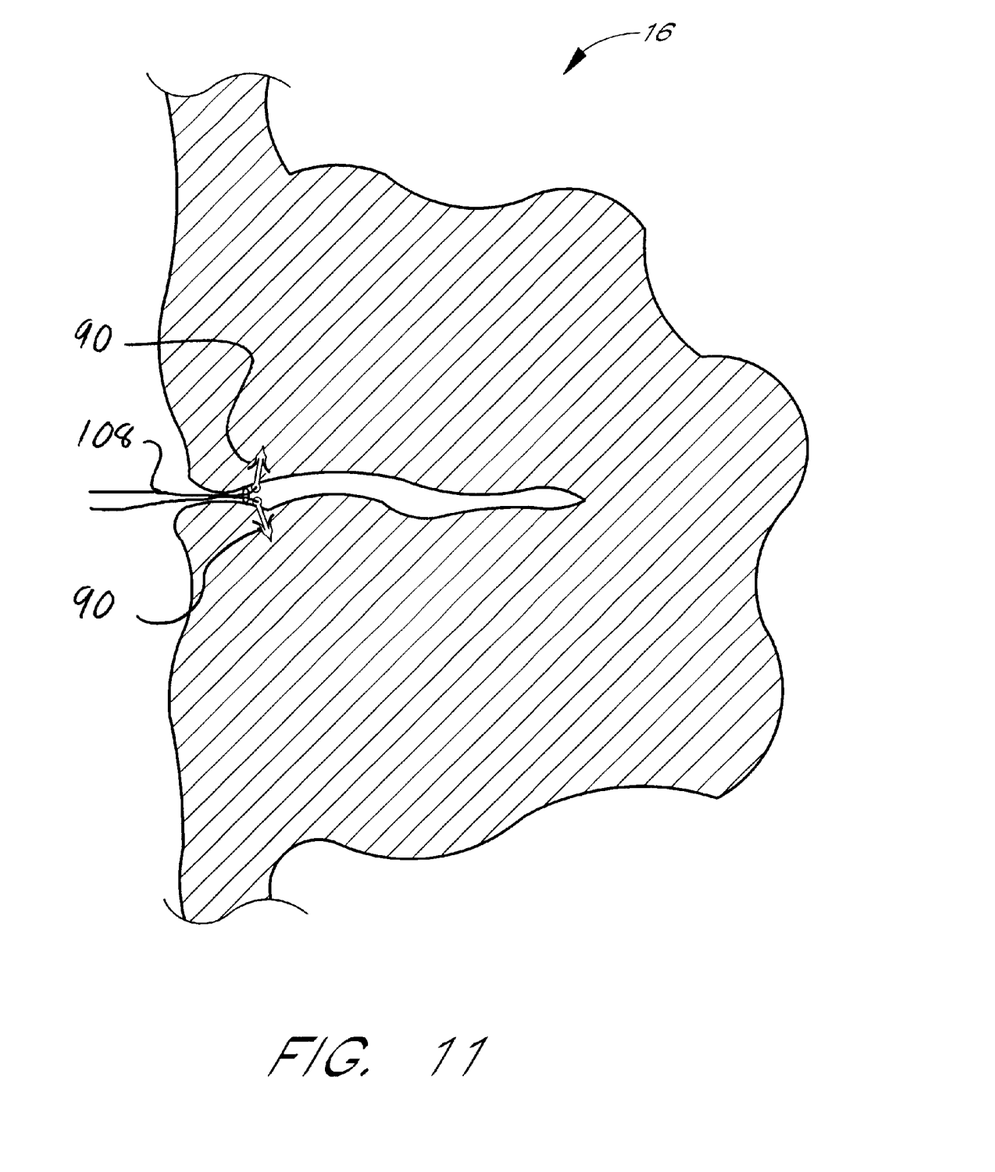
FIG. 11 is a schematic illustration as in FIG. 10, with the closure catheter retracted and the LAA drawn closed using the tissue anchors.

Following inclination of the anchor supports 62, the deployment wire 106 is proximally retracted thereby advancing each of the tissue anchors 90 into the surrounding tissue 10 as has been discussed. See FIG. 9. The anchor supports 62 are thereafter returned to the first, axial position, as illustrated in FIG. 10, for retraction from the left atrial appendage. Proximal retraction on the anchor sutures 108 such as through a tube, loop or aperture will then cause the left atrial appendage wall to collapse as illustrated in FIG. 11. Anchor sutures may thereafter be secured together using any of a variety of conventional means, such as clips, knots, adhesives, or others which will be understood by those of skill in the art. Alternatively, the LAA may be sutured, pinned, stapled or clipped shut, or retained using any of a variety of biocompatible adhesives.

In an alternate embodiment, a single suture is secured to a first anchor and slidably connected to the remainder of the anchors such that proximal retraction of the suture following deployment of the anchors draws the tissue closed in a "purse string" fashion. A similar technique is illustrated in FIGS. 31A and 31B in U.S. Pat. No. 5,865,791 to Whayne, et al., the disclosure of which is incorporated in its entirety herein by reference.

The foregoing closure techniques may be accomplished through the closure catheter, or through the use of a separate catheter. The closure catheter may thereafter be proximally retracted from the patient, and the percutaneous and vascular access sites closed in accordance with conventional puncture closure techniques.

Referring to FIGS. 12A–12G, there are illustrated a variety of tissue anchors which may be used in the tissue closure or attachment device of the present invention. Each of FIGS. 12A and 12B disclose an anchor having a body 92, a distal tip 101, and one or more barbs 94 to resist proximal movement of the anchor. An aperture 107 is provided to receive the anchor suture. The embodiments of FIGS. 12A and 12B can be readily manufactured such as by stamping or cutting out of flat sheet stock.

Figure 12A:
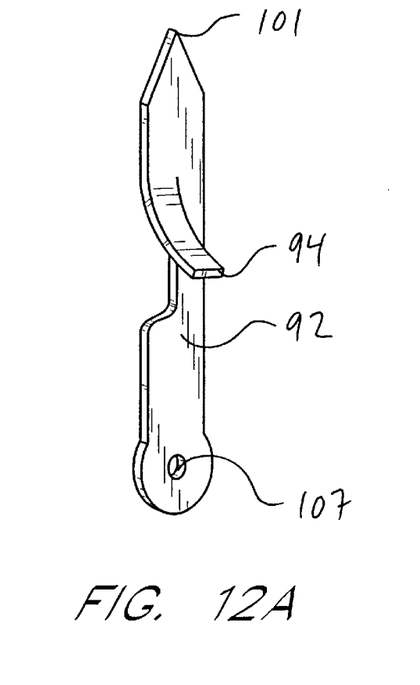
FIGS. 12A–12G are alternate tissue anchors for use with the closure catheter of the present invention.
Figure 12B:
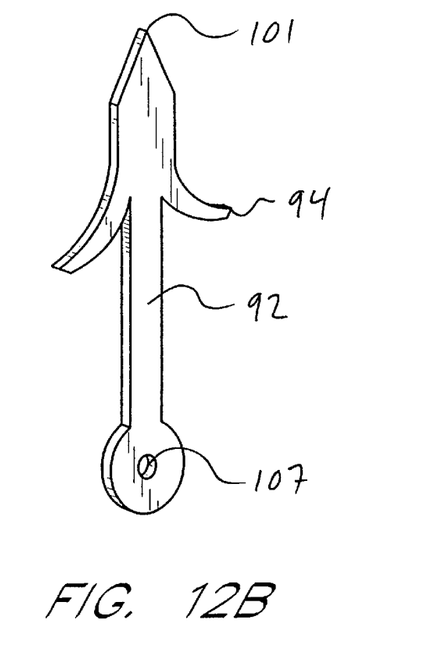
Figure 12C:
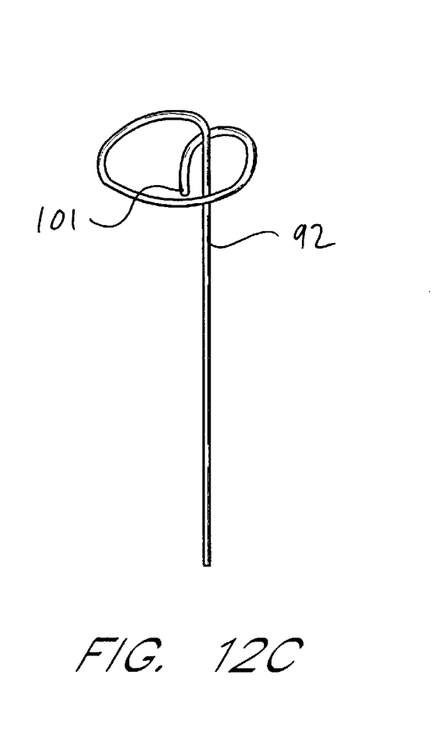

The anchor illustrated in FIG. 12C comprises a wire having a body 92 and a distal tip 101. The wire preferably comprises a super-elastic alloy such as Nitinol or other nickel titanium-based alloy. The anchor is carried within a tubular introducer, in a straight orientation, for introduction into the tissue where the anchor is to reside. As the body 92 is advanced distally from the carrier tube, the anchor resumes its looped distal end configuration within the tissue, to resist proximal retraction on the wire body 92.

Figure 12D:
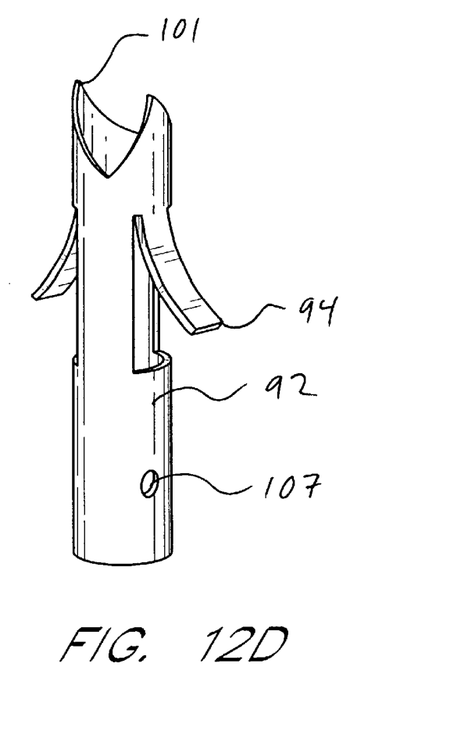

FIG. 12D illustrates a tubular anchor, which may be manufactured from a section of hypotube, or in the form of a flat sheet which is thereafter rolled about a mandrel and soldered or otherwise secured. The anchor comprises a distal tip 101, one or more barbs 94, and an aperture 107 for securing the anchor suture. The anchor of FIG. 12D may be carried by and deployed from the interior of a tubular anchor support as has been discussed. Alternatively, the anchor of FIG. 12D can be coaxially positioned over a central tubular or solid anchor support wire.

Figure 12E:
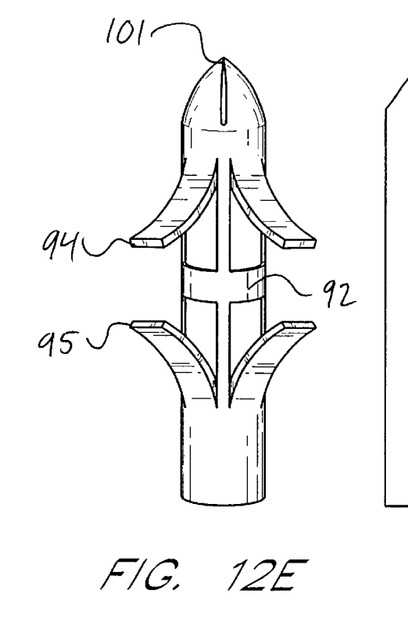
Figure 12F:
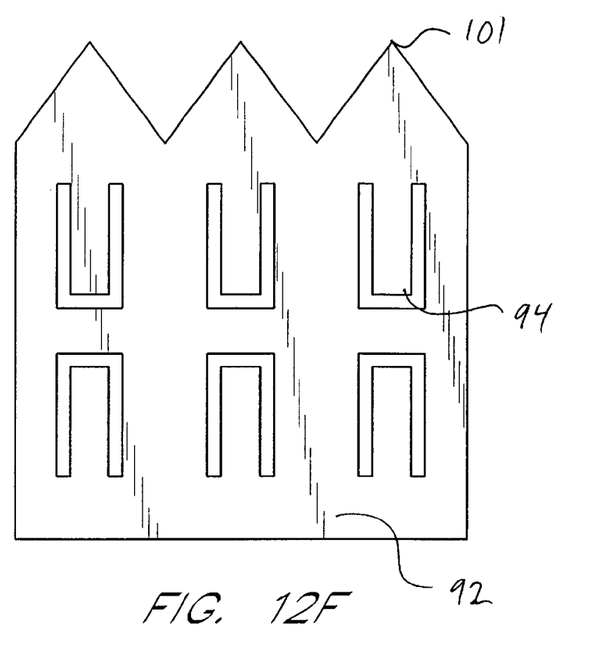
Figure 12G:
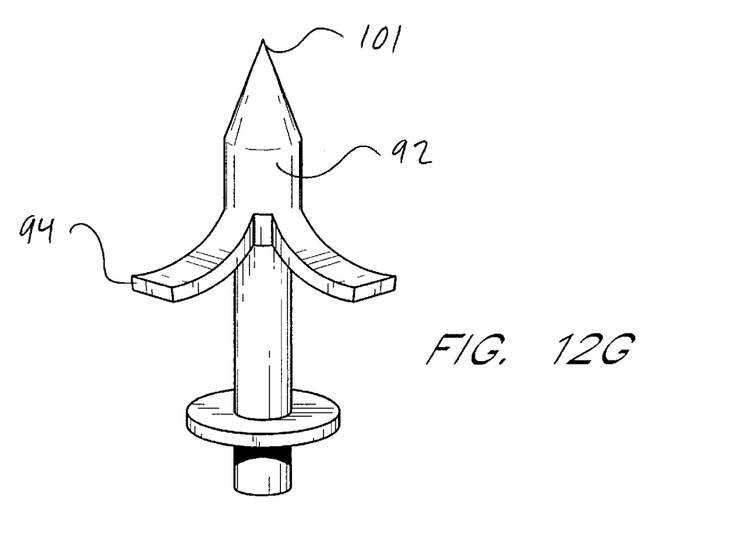

FIG. 12E illustrates an anchor which may be formed either by cutting from tube stock or by cutting a flat sheet such as illustrated in FIG. 2F which is thereafter rolled about an axis and soldered or otherwise secured into a tubular body. In this embodiment, three distal tips 101 in the flat sheet stock may be formed into a single distal tip 101 in the finished anchor as illustrated in FIG. 12E. One or more barbs 94 may be formed by slotting the sheet in a U or V-shaped configuration as illustrated. The anchor in FIG. 12E is additionally provided with one or more barbs 95 which resist distal migration of the anchor. This may be desirable where the anchor is implanted across a thin membrane, or in other applications where distal as well as proximal migration is desirably minimized.

Although the present invention has been described in terms of certain preferred embodiments, other embodiments will become apparent to those of skill in the art in view of the disclosure herein. Accordingly, the scope of the invention is not intended to be limited by the specific disclosed embodiments, but, rather, by the attached claims.

What is claimed is:

1. A method of reducing the volume of the left atrial appendage, comprising the steps of:

providing a catheter having at least four tissue anchors thereon, the anchors each having a suture secured thereto;

advancing the catheter through the heart and into the left atrial appendage;

inclining the anchors radially outwardly from the axis of the catheter towards tissue surrounding the opening to the left atrial appendage;

deploying the anchors from the catheter and into the tissue; and retracting the sutures to reduce the volume of the left atrial appendage.

2. A method as in claim 1, wherein the inclining step comprises proximally retracting a control for inclining anchor supports which carry the anchors.

3. A method as in claim 2, wherein proximally retracting the control axially compresses the anchor support.

4. A method as in claim 1, wherein the deploying the anchors step comprises proximally retracting a deployment line removably connected to each anchor.

* * * * *